US006387358B2

(12) United States Patent
Chuah et al.

(10) Patent No.: US 6,387,358 B2
(45) Date of Patent: May 14, 2002

(54) ANTIPERSPIRANT COMPOSITIONS

(75) Inventors: Beng Sim Chuah; Sarah Jane Clare; Kevin Ronald Franklin; Gordon Charles Hough; Graham Andrew Turner, all of Merseyside (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/759,123

(22) Filed: Jan. 12, 2001

(30) Foreign Application Priority Data

Jan. 14, 2000 (GB) ............................................. 0000875
Jul. 10, 2000 (GB) ............................................. 0016942

(51) Int. Cl.[7] .......................... A61K 7/32; A61K 7/34; A61K 7/38; A61K 7/00; A61K 31/76
(52) U.S. Cl. ........................... 424/65; 424/66; 424/68; 424/78.02; 424/78.08; 424/400; 424/401
(58) Field of Search ............................ 424/65, 66, 68, 424/78.02, 78.08, 400, 401

(56) References Cited

U.S. PATENT DOCUMENTS

| 4,425,328 A | 1/1984 | Nabial | |
| 4,937,069 A | 6/1990 | Shin | |
| 5,281,413 A | 1/1994 | Abrutyn et al. | 424/68 |
| 5,480,637 A | 1/1996 | Smith | 424/78.02 |
| 5,500,209 A | 3/1996 | Ross et al. | 424/66 |
| 5,635,165 A | 6/1997 | Panitch | 424/65 |
| 5,756,082 A | 5/1998 | Cashin et al. | 424/78.03 |
| 5,846,520 A | 12/1998 | Guskey et al. | 424/65 |
| 5,885,559 A | 3/1999 | Lee et al. | 424/65 |
| 6,045,814 A | 4/2000 | Roulier et al. | 424/401 |

FOREIGN PATENT DOCUMENTS

| WO | 95/18599 | 7/1995 |
| WO | 96/32924 | 10/1996 |
| WO | 97/11678 | 4/1997 |

OTHER PUBLICATIONS

Search Report under Section 17 Application No. GB 0000875.5 dated Jun. 27, 2000.
GB Search Report in a GB application GB 0008392.3.
PCT International Search Report in a PCT application PCT/EP 01/00186.

Primary Examiner—Shelley A. Dodson
(74) Attorney, Agent, or Firm—Kevin J. Stein

(57) ABSTRACT

Soft solid antiperspirant formulations in which a particulate antiperspirant active material is suspended in a continuous phase containing a water-immiscible liquid which is structured by specified proportions of an organic polymeric thickener and a second structurant selected from fibre-forming structurants and waxes (often other than fatty alcohols) or a mixture of both.

Such soft solid formulations avoid or minimise problems inherent in production of many published formulations such as sensitivity to small changes in concentration of the structurant.

20 Claims, No Drawings

ANTIPERSPIRANT COMPOSITIONS

FIELD OF THE INVENTION

The present invention relates to soft solid antiperspirant compositions for application to human skin, especially the axilla.

BACKGROUND OF THE INVENTION AND SUMMARY OF PRIOR ART

Antiperspirant compositions are widely used in order to enable their users to avoid or minimise wet patches on their skin, especially in axillary regions. A variety of these compositions make use of a thickened or structured liquid which is applied to the surface of the skin and serves as a carrier for the antiperspirant active. In many such compositions the liquid is water-immiscible and is thickened or structured by one or more materials incorporated into the composition for that purpose.

Antiperspirant formulations have been provided with a range of different product forms. One of these is a so-called "stick" which is usually a bar of an apparently firm solid material held within a dispensing container and which retains its structural integrity and shape whilst being applied. Another possibility is a softer solid composition accommodated in a dispensing container which in use extrudes the composition through one or more apertures.

The present invention is concerned with such soft solid compositions. Such compositions have sufficient rigidity that they are not observed by the human eye to flow, but they are deformable by hand pressure and can be extruded from a container through one or more apertures at the end of the container.

For use a small amount of the composition is extruded from the container, which may then be used as an applicator to spread the extruded material on the skin.

A number of properties of such compositions are significant. The composition should be stable and not leak from its container until deliberately extruded. Its sensory feel when applied should, desirably, not be sticky. The applied film of the composition preferably is of a transparent or translucent appearance rather than an opaque white. This property is referred to as low visible residue, and it is desirable in order that the deposit on the user's skin is not easily seen. Moreover, this also avoids conspicuous marks on clothing, to which the deposited material can accidentally transfer.

Soft solid antiperspirant compositions have been marketed. One commercial product used inorganic silica to thicken a carrier liquid. Some products currently on the market use mixtures of waxes to thicken a hydrophobic carrier liquid mixture. Such a formulation requires some complexity in its production process and careful control of temperature and other parameters at which the composition is put into containers for retail sale. The existing products structured with mixtures of waxes display some syneresis—that is to say weeping of liquid from the body of the composition.

Soft solid antiperspirant compositions with a continuous phase provided by water-immiscible liquid have also been disclosed in U.S. Pat. No. 5,635,165 (Panitch/Helene Curtis). The teaching of this document is that the structuring of antiperspirant compositions can be accomplished using either a sterol, such as lanosterol or a starch hydrolysate ester, such as dextrin palmitate.

The document states that to achieve the full advantage of its invention, a fatty alcohol should be included in an amount from 1 to 15% by weight of the composition, to adjust firmness and increase phase stability.

The examples in this document show two approaches to formulation. One is to use dextrin palmitate alone, or sterols alone, in an amount of 8% or more by weight of the composition. The alternative approach is to use a much smaller amount of such structuring agent accompanied by a larger amount of a fatty alcohol which is solid at room temperature of 20 C. One example [Ex 6] uses 1% dextrin palmitate with 2.8% sucrose distearate and 5.7% behenyl alcohol. Another example [Ex 16] uses 1% of a mixture of lanosterol and dihydrolanosterol, together with 1.25% sucrose distearate and 10% of behenyl alcohol. This document does not attempt to use lanosterol/dihydro-lanosterol jointly with dextrin palmitate and we have found that it would be impossible to do so. Lanosterol/dihydrolanosterol gives unstable compositions except with a restricted selection of carrier liquids (this is the subject of a copending application) but these liquids are such poor solvents for dextrin palmitate that it cannot be used to thicken them.

The thickening of organic liquids with polyamides in order to make antiperspirant compositions has been disclosed in U.S. Pat. No. 5,500,209. Typically, compositions exemplified in this document are thickened with 15% or more of thickening polymer, and are emulsions in which the antiperspirant active is dissolved in water or hydrophilic solvent.

U.S. Pat. No. 5,846,520 (Procter & Gamble) discloses compositions structured with a 12-hydroxystearic acid as a gelling agent. The document acknowledges that soft solid compositions may be made, although it prefers (and exemplifies) firm sticks. The document mentions possible optional components including waxes and fatty acid esters to be used in small percentages as nucleating agents.

12-hydroxystearic acid (12-HSA) is an example of materials which cause gelation by forming a network of fibres within the composition as it cools from a heated state during processing.

These materials can be used to make rigid sticks, as taught in U.S. Pat. No. 5,846,520 and other documents. However, we have found that if such a structurant is used to make a soft solid, the viscosity or hardness of the soft solid composition is very sensitive to small changes in the concentration of gelling agent, which is a potential difficulty when scaling up to commercial production. Also, complex processing is required similar to that required in making existing wax-structured soft solid products.

U.S. Pat. No. 5,480,637 (Dow Corning) used 12-hydroxystearic acid, together with an alkyl siloxane polymer or copolymer as a gelating system in order to produce solid products described as "firm" and "rigid". The examples use a range of alkyl methyl siloxane polymers but always at a concentration of only 1% by weight of the composition.

SUMMARY OF THE INVENTION

We have now found that advantageous soft solid antiperspirant compositions can be prepared by using a combination of a polymeric thickener and a second structurant in specified amounts which overall predominate over the amount (if any) of fatty alcohol which is solid at room temperature of 20° C.

Therefore, in a first aspect, this invention provides a soft solid antiperspirant composition having a continuous phase which contains water-immiscible liquid, and contains:
  i) 1.5 to 15%, preferably 1.5 to 10% by weight of the composition, of an organic polymeric thickener which is effective to increase the viscosity of the water-immiscible liquid;
  ii) 0.5 to 15%, preferably 0.5 to 10%, by weight of the composition, of second structuring material selected from the group consisting of
     a) structurant which forms a network of fibres within the continuous phase,
     b) waxes, other than fatty alcohols, which are solid at temperatures of 30° C. and below, but melt below 95° C., and
     c) mixtures thereof; and a particulate antiperspirant active in suspension in said continuous phase.

It will be appreciated that compositions according to this invention contain at least two materials serving to thicken/structure the composition.

In many instances the total amount of the organic polymeric thickener and second structuring material will be greater than the total amount of any fatty alcohol which is solid at 20° C.

If structurant (a) which forms a network of fibres within the continuous phase is present, the amount of it will generally be from 0.5 to 7% by weight of the composition.

If wax (b) is present the amount of it will generally be from 0.5 to 15% by weight of the composition.

A composition of this invention will generally be marketed in a container by means of which it can be applied at time of use. This container may be of conventional type.

A second aspect of the invention therefore provides an antiperspirant product comprising a dispensing container having at least one aperture for outflow of the contents of the container and a composition of the first aspect of the invention in the container. The aperture or apertures for outflow from the container will normally be of smaller cross section than the container. Means for urging the contents of the container to the said aperture or apertures, for flow through them, may be moving parts operable by the user or may simply be flexible container walls so that the user can expel composition from the container by squeezing it.

Compositions embodying the present invention can provide one or more of several advantages, and avoid disadvantages observed with other structuring systems.

The viscosity enhancing effect of the second structuring material is reduced markedly when the composition is applied. The thickening effect of the polymer is not altered so much at the time of application.

It is possible to formulate compositions which have adequate firmness while in a container prior to use, but which also have adequate mobility while being applied to skin. Moreover, the compositions can feel less sticky than compositions with a different thickening system.

By using this combination of organic polymeric thickener and other structuring material, it is possible to achieve a good combination of structural properties with a composition that gives only a low visible residue on skin and, also important, on clothing to which the composition may be accidentally transferred.

There is no necessity to incorporate any fatty alcohol which is solid at room temperature. Preferably such fatty alcohol is excluded or used only at low concentrations, since it is known to crystallize as relatively large platelets and increase the opacity and visibility of deposits.

A further advantage is simplicity of manufacture. The compositions of this invention can be made and packed by heating their constituents to form a liquid composition, mixing at temperatures where the composition is freely mobile, putting the composition into containers for retail sale and cooling or allowing these compositions to cool to room temperature. There is no need for continued stirring while the composition is thickening as it cools, and the temperature at which the composition is put into the containers is less critical.

Therefore in a third aspect, this invention provides a method of making a composition as specified above, by steps of mixing the ingredients of the composition, and before or after complete mixing, heating the ingredients of the composition to a temperature at which the continuous phase is a mobile liquid in which the organic polymer thickener (i) and the second structuring material (ii) are dissolved, followed by introducing the composition, at a temperature at which it is mobile, into containers, and causing or allowing cooling of the containers, until the temperature of the composition in the containers has fallen below 30° C.

According to a fourth aspect of the present invention, there is provided a method for preventing or reducing perspiration on human skin comprising topically applying to the skin a composition as specified in the first aspect of this invention.

DETAILED DESCRIPTION AND EMBODIMENTS

As mentioned above, the invention requires both an organic polymeric thickener and another structurant within a water-immiscible liquid phase in which a particulate solid antiperspirant is suspended. Other materials may also be present depending on the nature of the composition. The various materials will now be discussed by turn and preferred features and possibilities will be indicated.

Water-immiscible Liquid

The water-immiscible liquid comprise one or a mixture of materials which are relatively hydrophobic so as to be immiscible in water. Some hydrophilic liquid may be included, provided the overall liquid mixture is immiscible with water. Generally, this liquid or liquid mixture (when in the absence of polymeric thickener or other structurant) will be freely mobile at temperatures of 15 C. and above. It may have some volatility but its vapour pressure will generally be less than 4 kPa (30 mmHg) at 25° C. so that the material can be referred to as an oil or mixture of oils. More specifically, it is desirable that at least 80% by weight of the liquid should consist of materials with a vapour pressure not over this value of 4 kPa at 25° C.

It is preferred that the liquid or liquid mixture includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa to 2 kPa at 25° C.

It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ m$^2$/sec (10 centistokes), and particularly above $10^{-7}$ m$^2$/sec (0.1 centistokes), the linear siloxanes normally exhibiting a viscosity of below $5\times10^{-6}$ m$^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic liquid employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include Dow Corning 556™ and Dow Corning 200™ series.

The water-immiscible liquid may contain from 0% to 100% by weight of one or more liquid silicones. Preferably, there is sufficient liquid silicone to provide at least 10%, better at least 15%, by weight of the whole composition. If silicone oil is used, volatile silicone preferably constitutes from 20 to 100% of the weight of the liquid or liquid mixture. In many instances, when a non-volatile silicone oil is present, its weight ratio to volatile silicone oil is chosen in the range of from 1:3 to 1:40.

Silicon-free hydrophobic liquids can be used instead of, or more preferably in addition to liquid silicones. Silicon-free hydrophobic organic liquids which can be incorporated include liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms. Although polyisobutene and polydecene are polymeric in nature, they are mobile liquids at room temperature of 20° C. and do not cause thickening of other hydrophobic oils.

Some hydrophobic aliphatic or aromatic esters are liquids which may be used. These also may well be used as only part of a liquid mixture.

Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable liquid aromatic esters, preferably having a melting point of below 20° C., include fatty alkyl benzoates. Examples of such esters include suitable $C_8$ to $C_{18}$ alkyl benzoates or mixtures thereof.

As mentioned above, aliphatic alcohols which are solid at 20 C., such as stearyl alcohol are preferably absent or else present in low concentration such as less than 5% by weight of the whole composition since these lead to visible white deposits when a composition is used.

However, aliphatic alcohols which are liquid at 20° C. may be employed. These include branched chain alcohols of at least 10 carbon atoms such as isostearyl alcohol and octyl dodecanol.

Silicon-free liquids can constitute from 0–100% of the water-immiscible liquid, but it is preferred that silicone oil is present and that the amount of silicon-free constituents preferably constitutes up to 50 or 60% and in many instances from 20 to 60% by weight of the liquid mixture.

Organic Polymeric Thickener

A number of organic polymers are effective to increase the viscosity of hydrophobic liquids, although some polymers do not do so.

A material which is suitable as an organic polymeric thickener will generally possess the following characteristics:

i) it will contain residues of at least 5 (possibly many more than 7) monomer units bonded together into a polymer chain ii) it should dissolve on heating in water-immiscible liquids, and specifically it must have a solubility of at least 1.5% by weight in the heated water-immiscible liquid of the continuous phase;

iii) after heating to dissolve and cooling to 20° C., it will increase the viscosity of the water-immiscible liquid of the continuous phase, in the absence of other structurant, when dissolved therein at the same concentration as in the formulation of the invention.

Preferably, under these conditions, it will bring about a viscosity increase of at least 100 mPa.sec, better at least 250 mPa.sec when viscosity is measured with a Brookfield viscometer using a T-bar spindle at 10 rpm at 20° C. The choice of a type B, type C or type D T-bar spindle will depend on the viscosity of the system being measured. Provided the spindle is appropriate to provide a viscosity measurement it will enable determination of an increase in viscosity brought about by the polymer.

An additional or alternative characterisation of a suitable polymer is that it can thicken the water-immiscible liquid to a viscosity of at least 10,000 mPa.sec, measured in the same way, when incorporated in the water-immiscible liquid at 15% by weight, in the absence of the other structurant.

The polymer will generally be solid at 20° C. One category of polymer which has been found suitable is a polysaccharide esterified with monocarboxylic acid containing at least 4 carbon atoms.

Preferred in this category is a dextrin fatty acid ester having the formula:

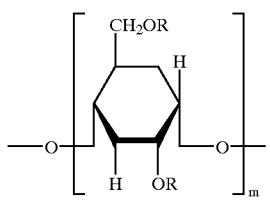

wherein each R group, individually, is a hydrogen atom or an acyl group having up to 22 carbon atoms, provided that at least one R group per glucose unit is an acyl group of at least 4 carbon atoms, and m has an average value from 5, 10 or 20 up to 50 or even up to 150, more preferably from 20 to 30. The dextrin fatty acid ester can be a partial ester, i.e. at least one R group is hydrogen; or the dextrin can be completely esterified, i.e., all R groups are acyl, such as a $C_4$–$C_{22}$ acyl group. The acyl groups may be the same or similar, and preferably they are straight chain acyl groups with chain lengths of 8 to 22 carbon atoms, e.g. in a range from 12 or 14 carbon atoms to 18 or 20 carbon atoms. Branched acyl groups may be included, possibly as in a mixture of $C_6$ to $C_{22}$ linear acyl groups. Shorter acyl groups may form part of a mixture, for example $C_4$ to $C_8$ acyl groups may be mixed with $C_{12}$ to $C_{22}$ linear acyl groups. In preferred embodiments, wherein the R group is a $C_8$–$C_{22}$ acyl group the degree of substitution is at least 2 (i.e., at least two R groups are $C_8$–$C_{22}$ acyl groups).

The $C_8$–$C_{22}$ fatty acids that are reacted with the starch hydrolyzate can be saturated or unsaturated acids, and include, for example, capric acid, pelargonic acid, caprylic acid, undecylic acid, undecylenic acid, lauric acid, myristic acid, pentadecylic acid, palmitic acid, heptadecylic acid, stearic acid, nonadecanoic acid, arachidic acid, oleic acid, linoleic acid, linolenic acid, similar acids, and mixtures thereof. These dextrin fatty acid esters are disclosed in Mori et al U.S. Pat. No. 4,780,145, incorporated herein by reference, and some of them are available under the trade name RHEOPEARL from Chiba Flour Milling Co., Ltd., Japan. An example of a dextrin fatty acid ester is dextrin palmitate, available commercially as RHEOPEARL KL and RHEOPEARL FL, for example, from Chiba Flour Milling Co., Ltd. Other examples of esters of $C_8$–$C_{22}$ carboxylic acids are dextrin behenate, dextrin laurate, dextrin myristate, dextrin stearate, and mixtures thereof.

A second category of polymer which can be used as a thickener is polyamides as discussed in U.S. Pat. No. 5,500,209. Such polyamides may be derived from organic diamines containing 2 to 12, preferably 2 to 8 carbon atoms, condensed with di- or poly carboxylic acids containing 4 to 20 carbon atoms per carboxylic acid group. Some monocarboxylic acid may be included in the reaction mixture to control polymer chain length. The dicarboxylic acids may be obtained by thermal polymerisation of unsaturated monocarboxylic acids.

Such polyamides are available from Henkel under their trade name VERSAMID. An example is VERSAMID 950 from hexamethylene diamine and adipic acid.

A further category of polymer which has been found useful is the block copolymers of styrene with ethylene, propylene and/or butylene available from Shell under their trade name KRATON G.

Preferred in this category is styrene ethylene/butylene styrene linear block copolymers e.g. that available as KRATON G 1726X.

Another suitable type of polymer is polymers of alpha methylstyrene and styrene available from Hercules under the trade name KRISTALEX. One suitable grade is KRISTALEX F85, with mean molecular weight of approximately 1200.

A further class of polymers found to be suitable for use with a second structurant comprises polyethylene having a molecular weight of from 500, sometimes 2000, to 8000, such as materials available from Quantum USI under the trade name MN 714.

A still further class of polymers found to be suitable comprises co-polymers of vinyl pyrrolidone with polyethylene containing at least 25 methylene units. A particularly suitable polymer comprises triacontanyl polyvinylpyrrolidone, such as that available from International Speciality Products under the trade name Antaron WP-660.

Yet another polymer found to be suitable although less preferred is alkyl substituted galactomannan available from Hercules under their trade name N-HANCE AG.

The thickening ability of polymers varies from one to another, which will affect the amount which is required. The amount will often lie in a range from 2% or 3% by weight of the composition up to 7% or more, such as to 10%, 12% or 15%.

Fibre-forming Structurant

A number of organic compounds are known to possess the ability to gel hydrophobic organic liquids such as water-immiscible hydrocarbon and/or silicone oils. Such materials are generally monomers or dimers with molecular weight below 10,000 often below 5,000 or even 1,000 rather than polymers with more than four repeat units or with molecular weight above 10,000.

Gel formation takes place as an exothermic event within a temperature range referred to as the gel point; upon reheating, melting of the gel takes place as an endothermic event within a temperature range. Such gels can be disrupted by shearing. Although a small partial recovery may then be observed, such gels do not recover their structure for a long time, if at all, unless remelted.

Materials with this ability to gel hydrophobic organic liquids have been reviewed by Terech and Weiss in "Low Molecular Mass Gelators of Organic Liquids and the Properties of their Gels" Chem. Rev 97, 3133–3159 [1997] and by Terech in Chapter 8, "Low-molecular weight Organogelators" of the book "Specialist surfactants" edited by I D Robb, Blackie Academic Professional, 1997.

It is characteristic of such structurants, useful in this invention, that:

if they are able to gel the organic liquid in the absence of any disperse phase, when used in sufficient quantity not exceeding 15% by weight;

the structured liquids are obtainable by cooling from an elevated temperature at which the structurant is in solution in the liquid—this hot solution being mobile and pourable;

the (thus obtained) structured liquid becomes more mobile if subjected to shear or stress;

the structure does not spontaneously recover within 24 hours if the sheared liquid is left to stand at ambient laboratory temperature, even though a small partial recovery may be observed;

the structure can be recovered by reheating to a temperature at which the structurant is in solution in the liquid and allowing it to cool back to ambient laboratory temperature.

It appears that such structurants operate by interactions which are permanent unless disrupted by shear or heating. Such structurants form a network of strands or fibres extending throughout the gelled liquid. In some cases these fibres can be observed by electron microscopy, although in other cases the observation of the fibres which are believed to be present is prevented by practical difficulties in preparing a suitable specimen. When observed, the primary fibres in a gel are generally thin (diameter less than 0.5 μm, often less than 0.2 μm) and appear to have numerous branches or interconnections. Primary fibres may entwine to form a thicker strand.

If these fibres are crystalline, they may or may not be the same polymorph as macroscopic crystals obtained by conventional crystallization from a solvent.

One material which is well known to form such gels is 12-hydroxy stearic acid which is discussed in Terech et al "Organogels and Aerogels of Racemic and Chiral 12-hydroxy octadecanoic Acid", Langmuir Vol 10, 3406–3418, 1994. The material is commercially available from Ajinomoto and also from Caschem.

U.S. Pat. No. 5,750,096 is one of several documents which teaches that gelation can be brought about using esters or amides of 12-hydroxy stearic acid. The alcohol used to form such an ester or the amine used to form such an amide may contain an aliphatic, cycloaliphatic or aromatic group with up to 22 carbons therein. If the group is aliphatic it preferably contains at least three carbon atoms. A cycloaliphatic group preferably contains at least five carbon atoms and may be a fixed ring system such as adamantyl.

Other fatty acids with $C_8$ or longer alkyl chains may be used and amides thereof can also be used. A specific example is lauric monoethanolamide also termed MEA lauramide:

N-acyl amino acid amides and esters are also known to structure liquids. We have established that they do so by forming fibrous networks. They are described in U.S. Pat. No. 3,969,087. N-Lauroyl-L-glutamic acid di-n-butylamide is commercially available from Ajinomoto under their designation GP-1.

Further materials which have been disclosed as gelling agents are the amide derivatives of di and tribasic carboxylic acids set forth in WO 98/27954 notably alkyl N,N'dialkyl succinamides.

Lanosterol, as disclosed in U.S. Pat. No. 5,635,165 mentioned above may suitably be used if the water-immiscible liquid is silicone oil and provided the polymeric thickener is sufficiently soluble therein. Lanosterol has the following chemical formula:

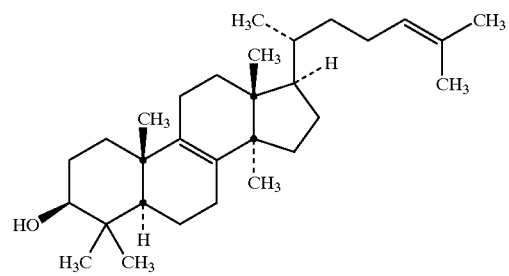

It is commercially available, e.g. from Croda Chemicals Ltd, and as supplied it contains some dihydrolanosterol. This impurity in the commercial material does not need to be removed.

A structurant which is the subject of a co-pending application is a combination of a sterol and a sterol ester.

In its preferred form the sterol satisfies either of the two formulae:

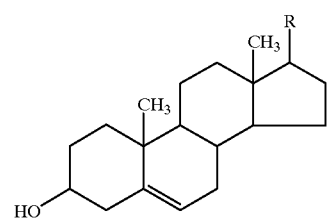

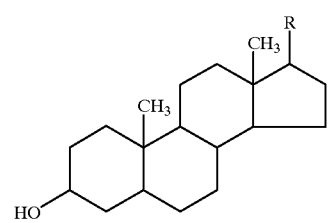

in which R represents an aliphatic, cycloaliphatic or aromatic group, and preferably a linear or branched aliphatic saturated or unsaturated hydrocarbon group. R desirably contains from 1 to 20 carbons and preferably from 4 to 14 carbons.

It is particularly suitable to employ β-sitosterol or campesterol or cholesterol, or a hydrogenated derivative thereof, such as dihydrocholesterol, or a mixture of two or more of them. An especially preferred sterol β-sitosterol.

The preferred sterol ester is oryzanol, sometimes referred to as γ oryzanol which contains material satisfying the following formula:

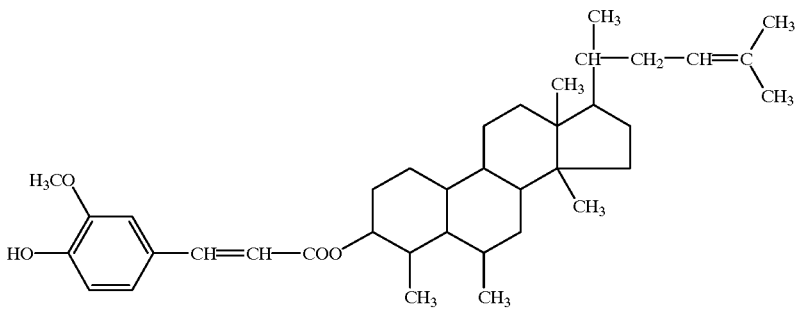

The sterol and sterol ester are used in a mole ratio that is normally selected in the range of from 10:1 to 1:10, especially from 6:1 to 1:4 and preferably in the range of from 3:1 to 1:2. Employment of the two system constituents within such a mole ratio range, and especially within the preferred range facilitates the co-stacking of the constituents and consequently facilitates the formation of a network that is readily able to structure the formulation.

Another structurant which is the subject of a co-pending application and which may be used in this invention is an ester of cellobiose and a fatty acid, preferably of 6 to 13 carbon atoms especially 8 to 10 carbon atoms. Preferably the cellobiose is fully esterified, or nearly so, and is in the α-anomeric form.

The structure of such a compound, in its a-anomeric form is:

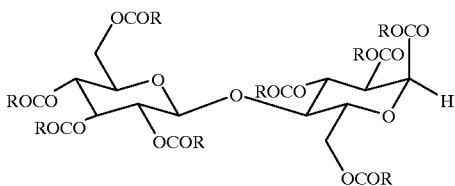

where R is an alkyl or alkenyl chain of 5 to 12 carbon atoms so that the acyl group contains 6 to 13 carbon atoms. Particularly preferred acyl groups incorporate a linear alkyl chain of 7 to 9 carbon atoms and are thus octanoyl, nonanoyl or decanoyl.

The acyl groups may have a mixture of chain lengths but it is preferred that they are similar in size and structure. Thus it is preferred that all of the acyl groups are aliphatic and at least 90% of the acyl groups have a chain length within a range such that the shorter and longer chain lengths in the range differ by no more than two carbon atoms, i.e. length in a range from m−1 to m+1 carbon atoms where m has a value in a range from 7 to 10.

Linear aliphatic acyl groups may be obtained from natural sources, in which case the number of carbon atoms in the acyl group is likely to be an even number or may be derived synthetically from petroleum as the raw material in which case both odd and even numbered chain lengths are available.

Synthetic methods for the esterification of saccharides are well known. The esterification of cellobiose has been reported by Takada et al in *Liquid Crystals,* (1995) Volume 19, pages 441–448. This article gives a procedure for the production of the alpha anomers of cellobiose octa-alkanoates by esterification of β-cellobiose using an alkanoic acid together with trifluoracetic anhydride.

A further example of structurant which is the subject of a co-pending application is compounds of the following general formula (T1):

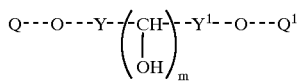

It is preferred that m is 2 so that the structurant compounds comply with a general formula (T2):

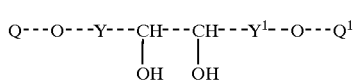

The groups Y and $Y^1$ will usually be identical, i.e. both methylene or both carbonyl. The groups Q and $Q^1$ may not be the same but often will be identical to each other.

If m is 2 and Y and $Y^1$ are methylene groups, the compound is a derivative of threitol, which is 1,2,3,4-tetrahydroxybutane, while if m is 2 and Y and $Y^1$ are carbonyl groups, the compound is a diester of tartartic acid, which is 2,3-dihydroxybutane-1,4-dioic acid.

It is preferred that each group Q and $Q^1$ contains an aromatic nucleus which may be phenyl or, less preferably, some other aromatic group. Thus Q and $Q^1$ may be groups of the formula

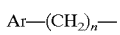

where Ar denotes an aromatic nucleus, notably phenyl or substituted phenyl and n is from 0 to 10.

An aromatic nucleus (Ar) is preferably unsubstituted or substituted with one or more substituents selected from alkyl, alkyloxy, hydroxy, halogen or nitro.

One substituent may be an alkyl or alkyloxy group with a long alkyl chain. Thus, a formula for preferred structurants of this invention can be given as (T3):

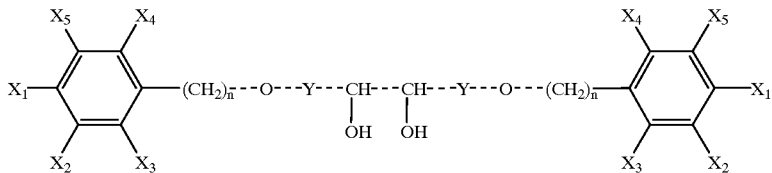

where
n=0 to 10, preferably 0 to 3, more preferably 1, 2 or 3;
Y=—CH$_2$— or >C=O
X$_1$=H, Cl, Br, F, OH, NO$_2$, O—R, or R, where R is an aliphatic hydrocarbon chain with 1 to 18 carbon atoms.
X$_2$ to X$_5$ are each independently H, Cl, Br, F, OH, NO$_2$, OCH$_3$, or CH$_3$ In these formulae above, the central carbon atoms which bear hydroxy groups are chiral centres. Thus, if m=2, Y and Y$^1$ are the same and Q and Q$^1$ are the same, the compounds will exist as R,R and S,S optically active forms as well as an optically inactive R,S form.

These compounds may be used as their optically active R,R or S,S forms or as a mixture of the two—which may be a racemic mixture.

Compounds within the general formula (TI) above are available commercially. Also, syntheses of these compounds have been given in scientific literature where the compounds were being used as intermediates for purposes not related to the present invention. Thus syntheses of threitol derivatives can be found in:

Kataky et al, J. Chem Soc Perkin Trans vol 2 page 321 [1990] Tamoto et al, Tetrahedron Vol 40 page 4617 [1984], and Curtis et al, J. C. S. Perkin I Vol 15 page 1756 [1977]. Preparations of tartrate esters are found at: Hu et al J. Am. Chem. Soc. Vol 118, 4550 [1996] and Bishop et al J. Org Chem Vol56 5079 [1991].

Waxes

This term "wax" is conventionally applied to a variety of materials and mixtures which have similar physical properties, namely that:
- they are solid at 30° C. and preferably also at 40° C.;
- they melt to a mobile liquid at a temperature above 30° C. but generally below 95° C. and preferably in a temperature range of 40° C. to 90° C.;
- they are water-insoluble and remain water-immiscible when heated above their melting point.

Waxes are usually hydrocarbons, silicone polymers, esters of fatty acids or mixtures containing such compounds along with a minority (less than 50%) of other compounds. Naturally occurring waxes are often mixtures of compounds which include a substantial proportion likely to be a majority of fatty esters.

Waxes form crystals in the water-immiscible liquid when it cools from the heated state during processing.

These crystals take various forms including needles and platelets depending on the individual waxes. Some waxes form a network of fibrous crystals and can therefore also be identified as fibre-forming structurants.

Examples of hydrocarbon waxes include paraffin wax, microcrystalline wax and polyethylenes with molecular weight of 500 to 10,000, often 2000 to 10,000.

Examples of ester waxes include esters of C$_{16}$–C$_{22}$ fatty acids with glycerol or ethylene glycol and these may be made synthetically.

Examples of natural waxes include beeswax, carnauba and candelilla waxes which are of vegetable origin and mineral waxes from fossil remains other than petroleum. Montan wax, which is an example of mineral wax, includes non-glyceride esters of carboxylic acids, hydrocarbons and other constituents.

Waxes useful in the present invention will generally be those found to thicken water-immiscible oils such as cyclomethicones when dissolved therein (by heating and cooling) at a concentration of 5 to 15% by weight.

If a wax is used which forms a network of fibres, the amount of it may be from 0.5 to 7% by weight of the composition. If a wax is used which does not form such a network, for instance a wax which crystallizes as spheralitic needles or as small platelets, the amount may well be from 2% or 3% up to 10%, 12& or 15% of the composition. Silicone waxes are an example of waxes which crystallize as small platelets.

The total amount of second structurant may range from 0.5% or 1% of the composition up to 9%, 10% or 15%.

The ratio of polymer to second structurant can vary considerably but in many instances it will lie in a range from 6:1 to 1:4.

In a number of embodiments the composition will contain 0.5 to 10% or 15% polymeric thickener, 0.5 to 7% of fibre-forming structurant and 2% to 10% of a wax such as silicone wax which does not crystallize as a network of fibres, all these percentages being by weight of the composition.

Some polymers, notably some polyethylenes have melting characteristics such that they will satisfy the definition of a wax. It is possible, within the scope of this invention for such a polymer to be present accompanied by a fibre-forming structurant and/or another wax. It is also possible for such a polymer to be present as a wax, when some other polymer is present.

Antiperspirant Actives

The composition will contain a particulate antiperspirant active. Antiperspirant actives are preferably incorporated in an amount of from 0.5–60%, particularly from 5 to 30% or 40% and especially from 5 or 10% to 30 or 35% of the weight of the composition.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y \cdot wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference.

Zirconium actives can usually be represented by the empirical general formula: $ZrO(OH)_{2n-nz}B_z \cdot wH_2O$ in which z is a variable in the range of from 0.9 to 2.0 so that the value 2n−nz is zero or positive, n is the valency of B, and B is selected from the group consisting of chloride, other halide, sulphamate, sulphate and mixtures thereof. Possible hydration to a variable extent is represented by wH20. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-phenylalanine, dl-valine, dl-methionine and -alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilised include astringent titanium salts, for example those described in GB 2299506A.

The proportion of solid antiperspirant salt in a composition normally includes the weight of any water of hydration and any complexing agent that may also be present in the solid active.

The particle size of the antiperspirant salts often falls within the range of 0.1 to 200 μm with a mean particle size often from 3 to 20 μm. Both larger and smaller mean particle sizes can also be contemplated such as from 20 to 50 μm or 0.1 to 3 μm.

Optional Ingredients

Optional ingredients in compositions of this invention can include deodorants, for example at a concentration of up to about 10% w/w. Suitable deodorant actives can comprise deoperfumes, and/or microbicides, including particularly bactericides, such as chlorinated aromatics, including biguanide derivatives, of which materials known as Triclosan e.g. Igasan DP300™, Tricloban™, and Chlorhexidine warrant specific mention. A yet another class comprises biguanide salts such as those available under the trade mark Cosmosil™.

Other optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

The compositions herein can incorporate one or more cosmetic adjuncts conventionally envisaged for antiperspirant soft solids. Such cosmetic adjuncts can include skin feel improvers, such as clays, silica, talc or finely divided polyethylene, for example in an amount of up to about 10%; skin benefit agents such as glycerol, allantoin or lipids, for example in an amount of up to 5%; skin cooling agents other than the already mentioned alcohols, such a menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

Product Packages

A composition of this invention will usually be marketed as a product comprising a container with a quantity of the composition therein, where the container has at least one aperture for the delivery of composition, and means for urging the composition in the container towards the delivery aperture(s). Conventional containers take the form of a barrel of oval cross section with an apertured part at one end of the barrel.

Generally the container will include a cap to go over that apertured end part and a component part which is sometimes referred to as an elevator or piston fitting within the barrel and capable of relative axial movement along it. The composition is accommodated in the barrel between the piston and the apertured part on the barrel. The piston is used to urge the body of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. Preferably the container also includes a transport mechanism for moving the piston comprising a threaded rod which extends axially into the body of the composition through a correspondingly threaded aperture in the piston, and means mounted on the barrel for rotating the rod. Conveniently the rod is rotated by means of a handwheel mounted on the barrel at its closed end, i.e. the opposite end to the delivery opening.

The apertured part at one end of the barrel is normally a closure with one or more apertures through which composition from the barrel can be extruded. The number and design of such apertures is at the discretion of the designer of the package.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

Preparation

Compositions of this invention can be produced by conventional processes for making suspension solids or soft-solids. Such processes involve forming a heated mixture of the composition at a temperature which is sufficiently elevated that all the polymer and other structurant dissolves, introducing that mixture into a mould, which may be a dispensing container, and then allowing the mixture to cool.

A convenient process sequence for a composition, which is a suspension, comprises first forming a solution of the polymer and other structurant in the water-immiscible liquid or liquid mixture. This is normally carried out by agitating the mixture at a temperature sufficiently high that all the structurant dissolves (the dissolution temperature) such as a temperature in a range from 50 to 150° C. Thereafter the particulate constituent, for example particulate antiperspirant active, is blended with the hot mixture. This must be done slowly, or the particulate solid must be preheated, in order to avoid premature gelation. The resulting blend is then introduced into a dispensing container such as a stick barrel. This is usually carried out at a temperature 5 to 30° C. above the setting temperature of the composition. The container and contents are then cooled to ambient temperature. Cooling may be brought about by nothing more than allowing the container and contents to cool. Cooling may be assisted by blowing ambient or even refrigerated air over the containers and their contents.

Measurement of Properties i) Texture Analyser

This test apparatus can move a blunt probe into or out from a sample at a controlled speed and at the same time measure the applied force. The parameter which is determined as hardness is a function of the force and the projected area of indentation.

A specific test protocol used a Stable Micro systems TA.XT2I™ Texture Analyser. A sample of composition was made by heating the ingredients, pouring into a container and allowing to cool as described above. The container was a 15 ml glass jar with a wide mouth. A metal sphere, of diameter 9.5 mm, was attached to the underside of the *Texture Analyser's* 5 kg load cell such that it could be used for indenting a sample placed beneath it on the base plate of the instrument. After positioning the sample, the sphere position was adjusted until it was just above the sample surface. Texture Expert Exceed™ software was used to generate the subsequent motion profile used in the test method. This profile initially moved the sphere into contact with the sample and then indented the sphere into the sample at an indentation speed of 0.05 mm/s for a distance of 7 mm. At this distance the direction of motion of the sphere was immediately reversed to withdraw the sphere from the sample at the same speed of 0.05 mm/s. During the course of the test, the data acquired were time(s), distance (mm) and force (N) and the data acquisition rate was 25 Hz.

The data associated with each test were manipulated using standard spreadsheet software and used to calculate the hardness, H, at a travelled distance of 4.76 mm after initial contact with the sample, using the following equation:

$$H=F/A$$

(H expressed in $N.mm^{-2}$, F in N and A in $mm^{-2}$) where F is the load at the same travelled distance and A is the projected area of the indentation. This area can be calculated geometrically and is equal to the area of a diametral plane of the sphere, i.e. $\pi \times (4.76)^2$ $mm^2$.

For a soft solid composition the measured hardness H will generally be from 0.003 to 0.5 $N/mm^2$. Frequently, the hardness will be from 0.003 up to 0.1 $N/mm^2$.

ii) Whiteness of Deposit

Another test of the properties of a composition is the whiteness and hence opacity of the composition which is delivered onto a surface when the composition is drawn across that surface (representing the application of the composition to human skin). To carry out this test of deposition, a sample of the composition was first applied to a test fabric under standardised conditions.

The test fabric was a rectangular strip of black worsted wool fabric 9 cm by 15 cm. This was placed in an apparatus consisting of a metallic base onto which was hinged a metallic frame defining a rectangular aperture of 5 cm by 9 cm. The test portion of fabric was laid on the base. The hinged frame was placed over the fabric and secured to the base by means of two screws thereby clamping the test fabric in place but exposing an area of 5×9 cm through the aperture.

A sample of soft solid composition in a dispensing container was kept at ambient laboratory temperature (about 20 C.) before it was required for measurement. A portion of the composition is then extruded from the container through the dispensing apertures at one end. A weight amount (0.51 g) of the extruded composition was spread uniformly across the 5×9 cm area of test fabric enclosed by the frame. Spreading was carried out using a plastic spreading tool. After spreading the sample of composition on the fabric substrate, it was removed from the apparatus and weighed to check that the mass of applied sample was 0.5±0.01 gms.

The fabric with applied sample of composition was then assessed twice for whiteness, once after one hour and again after 24 hours.

This measurement was carried out using a Sony XC77™ monochrome video camera with a Cosmicar™ 16 mm focal length lens positioned vertically above a black table illuminated from a high angle using fluorescent tubes to remove shadowing. The apparatus was initially calibrated using a reference white card, after the fluorescent tubes had been turned on for long enough to give a steady light output. The cloth with a deposit thereon was placed on the table and the camera was used to capture an image. An area of the image of the deposit was selected and analysed using a Kontron IBAS™ image analyser. This notionally divided the image into a large array of pixels and measured the grey level of each pixel on a scale of 0 (black) to 255 (white). The average of the grey intensity was calculated. This was a measure of the whiteness of the deposit, with higher numbers indicating a whiter deposit. It was assumed that low numbers show a clear deposit allowing the substrate colour to be seen. All samples were prepared in triplicate and a mean of the three measured values was reported.

The above test procedures were applied to two soft solid compositions currently marketed commercially. An existing product structured with castor wax and a silicone wax had a hardness measured by texture analyser of 0.0231, a whiteness measurement after 1 hour of 23 and a whiteness measurement after 24 hours of 42. A competitor's product, believed also to have a wax structuring system, had a hardness of 0.0318, a whiteness measurement after 1 hour of 20 and a whiteness measurement after 24 hours of 83.

EXAMPLES

The examples and comparative examples set out in the series of tables below were prepared using a number of materials whose suppliers and some other details are given in the following list. Throughout these tables, the amounts of the materials are percentages by weight.

1. Dextrin palmitate (Rheopearl™ KL) from Chiba Flour Milling Co. under their trademark
2. Silicone wax (SF1642™) from General Electric Inc
3. Silicone wax (SF1632™) from General Electric Inc
4. Silicone wax (DC X2–2493™) from Dow Corning Inc
5. Silicone wax (1205-04-261) from General Electric
6. Silicone wax (Abilwax™ 9810) from Goldschmidt
7. Silicone wax (AMS-C30™) from Dow Corning Inc
8. Volatile cyclic silicone (cyclomethicone) (DC 345™) from Dow Corning
9. $C_{12}$–$_{15}$ alkylbenzoate (Finsolv™ TN) from Finetex
10. Al/Zr Tetrachlorohydrex glycine complex (AZAG-7167™) from Summit
11. Isopropyl palmitate (Estol™ 1517) from Unichema
12. Isostearyl alcohol (Prisorene™ 3515) from Unichema
13. Castorwax MP80™ from Caschem
14. Beeswax ester K62™ from Koster Keunen
15. $C_{18}$–$C_{36}$ fatty acid triglyceride, available as Syncrowax™ HGLC from Croda Chemicals
16. Behenic acid triglyceride, available as Syncrowax™ HRC from Croda Chemicals
17. Ethylene-vinyl acetate copolymer AC 400™ from Allied Sigma
18. Victory amber wax (a wax of vegetable origin) from Bareco
19. MN 714™ from Quantum USI
20. Polypropyleneglycol-14-butylether (Fluid™ AP) from Union Carbide
21. Isohexadecane, available as Permethyl™ 101A from Presperse
22. Mackamide™ (stearyl monoethanolamide) from McIntyre Group
23. Mackamide™ LMM (lauryl monoethanolamide) from McIntyre Group
24. Eutanol™ G from Henkel
25. 12-HSA from Caschem
26. β-sitosterol from Kaukas
27. Oryzanol from Jan Dekker
28. N-Lauroyl-glutamic acid di-n-butylamide, available as GP-1™ from Ajinomoto
29. $C_{18}$–$C_{36}$ fatty acid glycol ester, available as Syncrowax™ ERLC from Croda Chemicals
30. Kristalex F85 Hydrocarbon resin from Hercules
31. N-Hance AG 50™ alkyl substituted galactomannan from Hercules
32. Kraton™ G 1726 block copolymer from Shell
33. Versamid™ 930 polyamide from Henkel
34. Suprafino™ A talc (particle size about 5) from Cyprus Minerals
35. Polyethylene beads, available as Acumist™ B9 from Allied Sigma
36. Polyethylene beads, available as Acumist™ C9 from Allied Sigma
37. Microcrystalline wax, available as Permulgin™ 4201 from Koster Keunen
38. Volatile cyclic silicone (cyclomethicone) DC 245™ from Dow Corning
39. Triacontenyl vinyl pyrrolidone copolymer, available as Antaron™ WP-660 from ISP.

The following general method of preparation was used for these examples. A solution of the thickening polymer and other structurants in the organic liquid(s) was made by mixing these materials, heating and agitating the mixture at a temperature sufficiently high that the polymer and other structurants all dissolve. The mixture was then allowed to cool to 80–85° C. before the aluminium-containing antiperspirant active was added. The mixture was next allowed to cool to 5–20° C. above its gelling temperature (determined in a preliminary experiment) and poured into dispensing containers for soft solids. These were then left to cool to room temperature.

The procedure was varied slightly in two instances. If GP-1 was used, it was first dissolved in the hot liquid mixture after which the thickening polymer and any other structurants were added and dissolved. If β-sitosterol and oryzanol were used in combination as structurant, the oryzanol was first dissolved in the hot liquid mixture followed by addition and dissolution of the thickening polymer, β-sitosterol and any other structurants. In both of these variations, the general procedure then continued as stated above with cooling to 80–85° C. for addition of the antiperspirant active, further cooling to 5–20° C. above the gelling temperature (determined previously) and pouring into dispensing containers.

Determinations of whiteness and hardness were done by the methods given earlier. All temperatures are in degrees Celsius.

| A) Dextrin palmitate compared with Dextrin palmitate + Silicone wax combinations | | | | | | |
|---|---|---|---|---|---|---|
| Ingredients (% by weight) | Ex. 1 comp. | Ex. 2 | Ex. 3 | Ex. 4 | Ex. 5 | Ex. 6 |
| Dextrin palmitate (1) | 10 | 5 | 5 | 5 | 5 | 5 |
| Silicone wax SF 1632 (3) | — | 5 | — | — | — | — |
| Silicone wax | — | — | 5 | — | — | — |

-continued

A) Dextrin palmitate compared with Dextrin palmitate + Silicone wax combinations

| Ingredients (% by weight) | Ex. 1 comp. | Ex. 2 | Ex. 3 | Ex. 4 | Ex. 5 | Ex. 6 |
|---|---|---|---|---|---|---|
| DC X2-2493 (4) | | | | | | |
| Silicone wax GE 1205-04-261 (5) | — | — | — | 5 | — | — |
| Silicone wax Abilwax 9810 (6) | — | — | — | — | 5 | — |
| Silicone wax AMS-C30 (7) | — | — | — | — | — | 5 |
| Cyclomethicone (8) | 50.8 | 50.8 | 50.8 | 50.8 | 50.8 | 50.8 |
| C12–15 Alkyl benzoate (9) | 12.7 | 12.7 | 12.7 | 12.7 | 12.7 | 12.7 |
| AZAG 7167 (10) | 26.5 | 26.5 | 26.5 | 26.5 | 26.5 | 26.5 |
| Characterisation | | | | | | |
| hardness (N/mm$^2$) | 0.0262 | 0.0077 | | 0.0082 | 0.0066 | 0.0067 |
| Whiteness measurement (1 h) | 13 | 13 | 15 | 12 | 17 | 17 |
| Whiteness measurement (24 h) | 11 | 9 | 17 | 13 | 14 | 34 |

The compositions of Examples 2 to 7 were observed to break down when applied to skin after extrusion from a dispensing container; this extrudate could be rubbed into skin easily.

The composition of comparative Example 1 was harder. It did not break down as readily and was harder to rub into skin.

B) Dextrin palmitate + Silicone wax in different oil combinations

| Ingredients (% by weight) | Ex 7 | Ex 8 | Ex 9 | Ex 10 |
|---|---|---|---|---|
| Dextrin palmitate (1) | 5 | 5 | 5 | 8 |
| Silicone wax SF 1642 (2) | 5 | 5 | 5 | 2 |
| Cyclomethicone (8) | 50.8 | 50.8 | 50.8 | 50.8 |
| C$_{12-15}$ Alkyl benzoate (9) | 12.7 | — | — | 12.7 |
| Isopropyl palmitate (11) | — | 12.7 | — | — |
| Isostearyl alcohol (12) | — | — | 12.7 | — |
| AZAG 7167 (10) | 26.5 | 26.5 | 26.5 | 26.5 |
| Characterisation | | | | |
| Hardness (N/mm$^2$) | 0.0053 | 0.0079 | 0.0069 | 0.0171 |
| Whiteness measurement (1 h) | 14 | 12 | 12 | 12 |
| Whiteness measurement (24 h) | 14 | 10 | 10 | 10 |

Compositions of Examples 7 to 9 broke down and could be rubbed into skin easily. The composition of Example 10 was harder, but not as hard as that of comparative Example 1.

C) Dextrin palmitate + wax combinations

| Ingredients (% by weight) | Ex. 11 | Ex. 12 | Ex. 13 | Ex. 14 | Ex. 15 | Ex. 16 |
|---|---|---|---|---|---|---|
| Dextrin palmitate (1) | 5 | 5 | 5 | 5 | 5 | 5 |
| Castorwax MP80 (13) | 5 | — | — | — | — | — |
| Beeswax K62 (14) | — | 5 | — | — | — | — |
| Syncrowax HGLC (15) | — | — | 5 | — | — | — |
| Syncrowax HRC (16) | — | — | — | 5 | — | — |
| Vinyl acetate copolymer (17) | — | — | — | — | 5 | — |
| Victory Amber Wax (18) | — | — | — | — | — | 5 |
| Cyclomethicone (8) | 50.8 | 50.8 | 50.8 | 50.8 | 44.5 | 50.8 |
| C12–15 Alkyl benzoate (9) | 12.7 | 12.7 | 12.7 | 12.7 | 19.0 | 12.7 |
| AZAG 7167 (10) | 26.5 | 26.5 | 26.5 | 26.5 | 26.5 | 26.5 |
| Characterisation | | | | | | |
| hardness (N/mm$^2$) | 0.0272 | 0.0108 | 0.0086 | 0.0087 | 0.0065 | 0.0054 |
| Whiteness measurement (1 h) | 14 | 18 | 13 | 15 | 14 | 12 |
| Whiteness measurement (24 h) | 15 | 13 | 14 | 16 | 10 | 11 |

The compositions of Examples 11 to 16 once again broke down and could be rubbed into skin easily, even though the hardness of the (unextruded) composition of Example 11 was about the same as that of comparative Example 1.

| D) Dextrin palmitate with various waxes in various liquid mixtures | | | | | | | | |
|---|---|---|---|---|---|---|---|---|
| Ingredients (% by weight) | Ex. 17 | Ex. 18 | Ex. 19 | Ex. 20 | Ex. 21 | Ex. 22 | Ex. 23 | Ex. 24 |
| Dextrin palmitate (1) | 5 | 5 | 5 | 5 | 5 | 5 | 5 | 5 |
| Beeswax ester K62 (14) | 5 | — | — | 5 | — | 5 | — | — |
| Syncrowax HGLC (15) | — | 5 | — | — | 5 | — | — | — |
| Syncrowax HRC (16) | — | — | 5 | — | — | — | 5 | — |
| Polyethylene wax (19) | — | — | — | — | — | — | — | 5 |
| Cyclomethicone (8) | 50.8 | 50.8 | 50.8 | 50.8 | 50.8 | 50.8 | 50.8 | — |
| Isostearyl alcohol (12) | 12.7 | 12.7 | 12.7 | — | — | — | — | — |
| Alkyl benzoate (9) | — | — | — | — | — | — | — | 63.5 |
| PPG-butyl ether (20) | — | — | — | 12.7 | 12.7 | — | — | — |
| Isohexadecane (21) | — | — | — | — | — | 12.7 | 12.7 | — |
| AZAG 7167 (10) | 26.5 | 26.5 | 26.5 | 26.5 | 26.5 | 26.5 | 26.5 | 26.5 |
| Characterisation | | | | | | | | |
| Hardness (N/mm²) | 0.0084 | 0.0093 | 0.0086 | 0.0143 | 0.0110 | 0.0086 | 0.0071 | 0.0186 |
| Whiteness measurement (1 h) | 19 | 14 | 15 | 21 | 17 | 19 | 15 | 12 |
| Whiteness measurement (24 h) | 17 | 12 | 14 | 19 | 15 | 19 | 15 | 11 |

| E) Dextrin palmitate with fatty amides | | | | |
|---|---|---|---|---|
| Ingredients (percent by weight) | Ex. 25 | Ex. 26 | Ex. 27 | Ex. 28 |
| Dextrin palmitate (1) | 5 | 4 | 3 | 3 |
| Mackamide SMA (22) | 3 | — | — | — |
| Mackamide LMM (23) | — | 3 | 3 | 3 |
| Cyclomethicone (8) | 52.4 | 53.2 | 54 | 54 |
| Octyldodecanol (24) | — | — | — | 13.5 |
| C12–15 Alkyl benzoate (9) | 13.1 | 13.3 | 13.5 | — |
| AZAG 7167 (10) | 26.5 | 26.5 | 26.5 | 26.5 |
| Characterisation | | | | |
| Hardness (N/mm²) | 0.0145 | 0.0507 | 0.0093 | 0.0147 |
| Whiteness measurement (1 h) | 19 | 17 | 15 | 19 |
| Whiteness measurement (24 h) | 45 | 33 | 24 | 30 |

| F) Dextrin palmitate with 12-hydroxystearic acid | | | | | |
|---|---|---|---|---|---|
| Ingredients (% by weight) | Ex. 29 | Ex. 30 | Ex. 31 | Ex. 32 | Ex. 33 |
| Dextrin palmitate (1) | 7 | 7 | 7 | 7 | 4 |
| 12-Hydroxystearic acid (25) | 3 | 3 | 3 | 3 | 6 |
| Cyclomethicone (8) | 50.8 | 50.8 | 50.8 | 50.8 | 50.8 |
| PPG-butyl ether (20) | 12.7 | — | — | — | — |
| Isohexadecane (21) | — | 12.7 | — | — | — |
| Isostearyl alcohol (12) | — | — | 12.7 | — | — |
| C12–15 Alkyl benzoate (9) | — | — | — | 12.7 | 12.7 |
| AZAG 7167 (10) | 26.5 | 26.5 | 26.5 | 26.5 | 26.5 |
| Characterisation | | | | | |
| Hardness (N/mm²) | 0.0194 | 0.0273 | 0.0166 | 0.0338 | 0.0581 |
| Whiteness measurement (1 h) | 17 | 16 | 13 | 14 | 18 |
| Whiteness measurement (24 h) | 42 | 35 | 13 | 13 | 27 |

| G) Dextrin palmitate with 12-hydroxystearic acid and wax or fatty amide | | | | | | | |
|---|---|---|---|---|---|---|---|
| Ingredients (% by weight) | Ex. 34 | Ex. 35 | Ex. 36 | Ex. 37 | Ex. 38 | Ex. 39 | Ex. 40 |
| Dextrin palmitate (1) | 3 | 3 | 2 | 2 | 3 | 3 | 2 |
| 12-Hydroxystearic acid (25) | 2 | 3 | 4 | 4 | 2 | 2 | 2 |
| Silicone wax SF 1642 (2) | 5 | 4 | — | — | — | — | — |
| Silicone wax AMS-C30 (7) | — | — | 5 | — | 5 | — | — |
| Silicone wax Abilwax 9810 (6) | — | — | — | 5 | — | — | — |
| Beeswax ester K62 (14) | — | — | — | — | — | 5 | — |
| Mackamide LMM (23) | — | — | — | — | — | — | 3 |
| Cyclomethicone (8) | 50.8 | 50.8 | 50 | 50 | 50.8 | 50.8 | 53.2 |
| C12–15 alkyl benzoate (9) | 12.7 | 12.7 | 12.5 | 12.5 | 12.7 | 12.7 | 13.3 |
| AZAG 7167 (10) | 26.5 | 26.5 | 26.5 | 26.5 | 26.5 | 26.5 | 26.5 |
| Characterisation | | | | | | | |
| Hardness (N/mm²) | 0.0072 | 0.0090 | 0.0353 | 0.0139 | 0.0079 | 0.0073 | 0.0014 |
| Whiteness measurement (1 h) | 14 | 16 | 18 | 20 | 18 | 20 | 17 |
| Whiteness measurement (24 h) | 13 | 18 | 39 | 22 | 43 | 43 | 16 |

| H) Dextrin palmitate with β-sitosterol and oryzanol | | | | | |
|---|---|---|---|---|---|
| Ingredients (% by weight) | Ex. 41 | Ex. 42 | Ex. 43 | Ex. 44 | Ex. 45 |

-continued

| | | | | | |
|---|---|---|---|---|---|
| Dextrin palmitate (1) | 4 | 3 | 7 | 7 | 7 |
| -sitosterol (26) | 0.5 | 1.5 | 1.5 | 1.5 | 1.5 |
| Oryzanol (27) | 0.5 | 1.5 | 1.5 | 1.5 | 1.5 |
| Silicone wax SF 1642 (2) | — | 4 | — | — | — |
| Cyclomethicone (8) | 54.8 | 50.8 | 50.8 | 50.8 | 50.8 |
| C12–15 Alkyl benzoate (9) | 13.7 | 12.7 | — | — | — |
| Isostearyl alcohol (12) | — | — | 12.7 | — | — |
| PPG-butyl ether (20) | — | — | — | 12.7 | — |
| Isohexadecane (21) | — | — | — | — | 12.7 |
| AZAG 7167 (10) | 26.5 | 26.5 | 26.5 | 26.5 | 26.5 |
| Characterisation | | | | | |
| Hardness (N/mm$^2$) | 0.0038 | 0.1233 | 0.0595 | 0.1539 | 0.1679 |
| Whiteness measurement (1 h) | 17 | 16 | 18 | 17 | 21 |
| Whiteness measurement (24 h) | 16 | 11 | 13 | 31 | 25 |

J) Dextrin palmitate with GP-1 and wax

| Ingredients (% by weight) | Ex. 46 | Ex. 47 | Ex. 48 | Ex. 49 | Ex. 50 | Ex. 51 | Ex. 52 | Ex. 53 |
|---|---|---|---|---|---|---|---|---|
| Dextrin palmitate (1) | 4 | 3 | 3 | 2 | 2 | 3 | 3 | 3 |
| GP1 (28) | 1 | 1 | 1 | 2 | 1.5 | 1 | 1 | 1 |
| Silicone wax SF 1642 (2) | — | — | 5 | 6 | 7 | — | — | — |
| Silicone wax AMS-C30 (7) | — | — | — | — | — | 5 | — | — |
| Silicone wax Abilwax 9810 (6) | — | — | — | — | — | — | 5 | — |
| Beeswax ester K62 (14) | — | — | — | — | — | — | — | 5 |
| DC345 (8) | 48 | 55.6 | 51.6 | 44.5 | 44.1 | 51.6 | 51.6 | 51.6 |
| Isostearyl alcohol (12) | 20.6 | — | — | 19.0 | — | — | — | — |
| Octyldodecanol (24) | — | 13.9 | 12.9 | — | 18.9 | 12.9 | 12.9 | 12.9 |
| AZAG 7167 (10) | 26.5 | 26.5 | 26.5 | 26.5 | 26.5 | 26.5 | 26.5 | 26.5 |
| Characterisation | | | | | | | | |
| Hardness (N/mm$^2$) | 0.0065 | 0.0142 | 0.0144 | 0.0264 | 0.0331 | 0.0261 | 0.0208 | 0.0143 |
| Whiteness measurement (1 h) | 17 | 16 | 18 | 16 | 14 | 19 | 17 | 19 |
| Whiteness measurement (24 h) | 12 | 14 | 13 | 12 | 11 | 12 | 17 | 24 |

K) Dextrin palmitate with GP-1 and wax or fatty acid amide

| Ingredients (% by weight) | Ex. 54 | Ex. 55 | Ex. 56 | Ex. 57 | Ex. 58 | Ex. 59 |
|---|---|---|---|---|---|---|
| Dextrin palmitate (1) | 2 | 3 | 3 | 3 | 3 | 3 |
| N-Lauroyl-glutamic acid di-n-butylamide (28) | 1 | 2 | 1 | 1 | 1 | 1 |
| Syncrowax HGLC (15) | 7 | 5 | — | — | — | — |
| Syncrowax HRC (16) | — | — | 5 | — | — | — |
| Syncrowax ERLC (29) | — | — | — | 5 | — | — |
| Syncrowax HRSC (30) | — | — | — | — | 5 | — |
| Mackamide LMM (23) | — | — | — | — | — | 3 |
| Cyclomethicone (8) | 44.5 | 44.5 | 51.6 | 51.6 | 51.6 | 53.2 |
| Octyldodecanol (24) | 19.0 | 19.0 | 12.9 | 12.9 | 12.9 | 13.3 |
| AZAG 7167 (10) | 26.5 | 26.5 | 26.5 | 26.5 | 26.5 | 26.5 |
| Characterisation | | | | | | |
| Hardness (N/mm$^2$) | 0.0155 | 0.1160 | 0.0178 | 0.0176 | 0.0081 | 0.0107 |
| Whiteness measurement (1 h) | 14 | 17 | 16 | 17 | 17 | 17 |
| Whiteness measurement (24 h) | 19 | 13 | 14 | 15 | 15 | 15 |

L) Thickening polymer with 12-hydroxystearic acid or wax

| Ingredients (percent by weight) | Ex. 60 | Ex. 61 | Ex. 62 | Ex. 63 |
|---|---|---|---|---|
| Kristalex F85 (polymer, 30) | 7 | — | — | — |
| N-Hance AG 50 (polymer, 31) | — | 3 | 3 | — |
| Kraton G 1726 (polymer, 32) | — | — | — | 3 |
| 12-Hydroxystearic acid (25) | 3 | 7 | — | — |
| Silicone wax GE 1205-04-261 (5) | — | — | 7 | 7 |
| Cyclomethicone (8) | 50.8 | 38.1 | 38.1 | 12.7 |
| C12–15 Alkyl benzoate (9) | 12.7 | — | — | — |
| Isostearyl alcohol (12) | — | 25.4 | 25.4 | 50.8 |
| AZAG 7167 (10) | 26.5 | 26.5 | 26.5 | 26.5 |
| Characterisation | | | | |
| Hardness (N/mm$^2$) | 0.0326 | 0.0351 | 0.0099 | 0.0421 |
| Whiteness measurement (1 h) | 13 | 13 | 11 | 13 |
| Whiteness measurement (24 h) | 14 | 11 | 10 | 13 |

M) Dextrin palmitate + wax + other additives

| Ingredients (% by weight) | Ex. 64 | Ex. 65 | Ex. 66 |
|---|---|---|---|

-continued

| | | | |
|---|---|---|---|
| Dextrin palmitate (1) | 5 | 5 | 5 |
| Silicone wax SF 1642 (2) | 5 | 5 | 5 |
| Cyclomethicone (8) | 49.2 | 49.2 | 49.2 |
| C12–15 Alkyl benzoate (9) | 12.3 | 12.3 | 12.3 |
| Talc (34) | 2 | — | — |
| Polyethylene beads B9 (35) | — | 2 | — |
| Polyethylene beads C9 (36) | — | — | 2 |
| AZAG 7167 (10) | 26.5 | 26.5 | 26.5 |
| Characterisation | | | |
| Hardness (N/mm$^2$) | 0.0051 | 0.0065 | 0.0083 |
| Whiteness measurement (1 h) | 14 | 14 | 14 |
| Whiteness measurement (24 h) | 12 | 11 | 11 |

All of Examples 17 to 66 broke down and could easily be rubbed into skin, even though some of them had a hardness, before extrusion, which exceeded that of Example 1.

N) Polyethylene compared with polyethylene + Silicone wax combinations

| Ingredients (% by weight) | Ex. 67 (comp.) | Ex. 68 | Ex. 69 | Ex. 70 | Ex. 71 | Ex. 72 |
|---|---|---|---|---|---|---|
| Polyethylene (19) | 5 | 3 | 3 | 3 | 3 | 3 |
| Silicone wax AMS-C30 (7) | — | 5 | — | — | 3 | — |
| GP-1 (28) | — | — | 1 | — | — | — |
| 12-hydroxystearic acid (25) | — | — | — | 3 | 2 | — |
| Microcrystalline wax (37) | — | — | — | — | — | 3 |
| Cyclomethicone (38) | 13.7 | 16.2 | 13.9 | 27.0 | 26.2 | 27.0 |
| C12–15 Alkyl benzoate (9) | 54.8 | 39.3 | 55.6 | 40.5 | 39.3 | 40.5 |
| AZAG 7167 (10) | 26.5 | 26.5 | 26.5 | 26.5 | 26.5 | 26.5 |
| Characterisation | | | | | | |
| Hardness (N/mm$^2$) | 0.0094 | 0.026 | 0.015 | 0.062 | 0.055 | 0.013 |
| Whiteness measurement (1 h) | 9 | 11 | 14 | 14 | 12 | 16 |
| Whiteness measurement (24 h) | 10 | 9 | 13 | 11 | 11 | 13 |

The compositions of Examples 68 to 72 were observed to break down when applied to skin after extrusion from a dispensing container; this extrudate could be rubbed into skin easily. The composition of comparative Example 67 had a less satisfactory feel when applied to skin. It did not break down as readily and was harder to rub into skin.

P) Vinylpyrrolidone copolymer alone and compared with combinations

| Ingredients (% by weight) | Ex. 73 (comp.) | Ex. 74 | Ex. 75 | Ex. 76 | Ex. 77 |
|---|---|---|---|---|---|
| Triacontenyl PVP copolymer (39) | 10 | 5 | 5 | 5 | 3 |
| Lauramide MEA (23) | — | 5 | — | — | — |
| GP-1 (28) | — | — | 1 | 1.5 | 1 |
| Silicone wax | — | — | — | — | 4 |
| AMS-C30 (7) | | | | | |
| Cyclomethicone (38) | 50.8 | 50.8 | 54 | 53.6 | 52.4 |
| C12–15 Alkyl benzoate (9) | 12.7 | 12.7 | — | — | — |
| Octyldodecanol (24) | — | — | 13.5 | 13.4 | 13.1 |
| AZAG 7167 (10) | 26.5 | 26.5 | 26.5 | 26.5 | 26.5 |
| Characterisation | | | | | |
| Hardness (N/mm$^2$) | 0.003 | 0.072 | 0.013 | 0.033 | 0.051 |
| Whiteness measurement (1 h) | — | 18 | 13 | 12 | 17 |
| Whiteness measurement (24 h) | — | 17 | 14 | 12 | 26 |

The compositions of Examples 74 to 77 were observed to break down easily when applied to skin after extrusion from a dispensing container; this extrudate could be rubbed into skin easily. The composition of comparative Example 73 was too soft to use.

Q) Vinylpyrrolidone copolymer and wax combinations

| Ingredient (% by weight) | Ex. 78 (comp) | Ex. 79 | Ex. 80 | Ex. 81 |
|---|---|---|---|---|
| Triacontenyl PVP copolymer (39) | 5 | 5 | 5 | 5 |
| Syncrowax ERLC (12) | — | — | — | — |
| Silicone wax GE-1205-04-261 (5) | — | 4 | — | — |
| Microcrystalline wax (5) | — | — | — | 5 |
| Silicone wax AMS-C30 (7) | — | — | — | 5 |
| Cyclomethicone (38) | 51.6 | 51.6 | 50.8 | 50.8 |
| C12–15 Alkyl benzoate (9) | 12.9 | 12.9 | 12.7 | 12.7 |
| AZAG 7167 (10) | 26.5 | 26.5 | 26.5 | 26.5 |
| Characterisation | | | | |
| Hardness (N/mm$^2$) | 0.029 | 0.025 | 0.04 | 0.074 |
| Whiteness measurement (1 h) | 15 | 18 | 17 | 16 |
| Whiteness measurement (24 h) | 14 | 17 | 15 | 16 |

The compositions of these Examples 78 to 81 were also observed to break down easily when applied to skin after extrusion from a dispensing container; the extrudate could be rubbed into skin easily.

Comparative Examples 81 to 85

An attempt was made to prepare soft solid formulations using polymers as sole structurant, using the general method of preparation given above. The formulations are given in the table below.

R) Comparative examples with various polymers but no other structurants

| Ingredients (% by weight) | Ex. 82 | Ex. 83 | Ex. 84 | Ex. 85 |
|---|---|---|---|---|
| Kristalex F85 (polymer, 30) | 10 | — | — | — |
| N-Hance AG 50 (polymer, 31) | — | 10 | — | — |
| Kraton G 1726 (polymer, 32) | — | — | — | 10 |
| Versamid 930 (polymer, 33) | — | — | 10 | — |
| Cyclomethicone (8) | 50.8 | 38.1 | 12.7 | 12.7 |
| C12–15 alkyl benzoate (9) | 12.7 | — | — | — |
| Isostearyl alcohol (12) | — | 25.4 | 50.8 | 50.8 |
| AZAG 7167 (10) | 26.5 | 26.5 | 26.5 | 26.5 |

In these comparative examples polymers were used alone, but found to be unsuccessful. Example 82 separated into two phases. Examples 83 and 84 were sticky and elastic. Example 85 was very elastic and did not rub into skin.

Comparative Examples 86 to 89

An attempt was made to prepare soft solid compositions using a non-polymeric fibre-forming structurant without polymer. The method of preparation was very similar to the general method used for previous examples.

General Preparation Method

All were prepared by essentially the same method as for the polymer thickener containing systems. Details are given below.

A solution of the structurant in the organic liquid(s) was made by mixing these materials, heating and agitating the mixture at a temperature sufficiently high that the structurant dissolved. The mixture was then allowed to cool to 80–85 C. before the aluminium antiperspirant active was added. The mixture was next allowed to cool to 5–20 C. above its gelling temperature (determined in a preliminary experiment) and introduced into dispensing containers for soft solids. These were then left to cool to room temperature.

The formulations and their hardness determined by penetrometer are given in the following table:

| Ingredient (percentage by weight) | Ex. 86 | Ex. 87 | Ex. 88 | Ex. 89 |
|---|---|---|---|---|
| GP-1 | 1 | 1.5 | 2 | 5 |
| Cyclomethicone | 50.8 | 50.4 | 50.0 | 48.0 |
| Octyldodecanol | 21.7 | 21.6 | 21.5 | 20.5 |
| AZAG 7167 | 26.5 | 26.5 | 26.5 | 26.5 |
| Characterisation | | | | |
| Hardness (N/mm$^2$) | 0.007 | 0.038 | 0.034 | 0.165 |

Ex. 86 was very soft mixture and showed severe oil leakage.

Ex. 87 and 88 also leaked solvent.

Ex. 88 dispensed in the form of flakes rather than as a cream. It did not break down very easily when applied to skin and rub-in was difficult to achieve.

Ex. 89 was hard and dispensed in very flaky twirls. It was again difficult to break down and rub in.

Thus, none of these comparative examples was a satisfactory soft solid product.

Ex. 87 was probably the closest to a satisfactory composition. Even though Example 88 had almost the same hardness by penetrometer, it failed to disperse as a cream, and neither Examples 87 nor Example 88 was adequately stable.

what is claimed is:

1. An antiperspirant soft solid composition having a continuous phase which contains water-immiscible liquid, and contains
   i) 1.5 to 15%, by weight of the composition, of an organic polymer which is effective to increase the viscosity of the water-immiscible liquid;
   ii) second structuring material selected from the group consisting of
      a) 0.5 to 7% by weight of the composition of structurant which forms a network of fibres within the continuous phase,
      b) 0.5 to 15% by weight of the composition of waxes, other than fatty alcohols, which are solid at temperatures of 30 C. and below, but melt below 95 C., and
      c) mixtures thereof;
   iii) from 0 to 3%, by weight of the composition, of fatty alcohol which is solid at 20 C., with the proviso that the total amount of any said fatty alcohol is less than the total of said organic polymer (i) and second structuring material (ii); and
   a particulate antiperspirant active in suspension in said continuous phase.

2. A composition according to claim 1 wherein the total amount of any said fatty alcohol which is solid at 20 C. is from 0 to 1.5% by weight of the composition.

3. A composition according to claim 1 wherein the total amount of said organic polymer (i) and second structuring material (ii) is from 3% to 15% by weight of the composition.

4. A composition according to claim 1 wherein the total amount of said organic polymer (i) and second structuring material (ii) is from 4% to 12% by weight of the composition.

5. A composition according to claim 1 wherein the total amount of second structuring material is from 1% to 9% by weight of the composition.

6. A composition according to claim 1 wherein the second structuring material comprises from 3 to 8% of wax which is solid at temperatures of 40° C. and below, but melts below 90° C.

7. A composition according to claim 5 wherein the second structuring material comprises from 1% to 6% by weight of the composition of structurant which forms a network of fibres and/or from 3% to 7% by weight of the composition of said wax.

8. A composition according to claim 1 wherein the organic polymeric thickener comprises from 2 to 7% by weight of the composition of a polysaccharide esterified with a monocarboxylic acid of 8 to 22 carbon atoms.

9. A composition according to claim 1 wherein the organic polymeric thickener comprises from 3 to 12% by weight of the composition of a polymer selected from the group consisting of polyamides and hydrocarbon polymers.

10. A composition according to claim 1 wherein the organic polymer thickener comprises from 2 to 12% by weight of the composition of a co-polymer of vinyl pyrrolidone and polymethylene blocks which contain at least 25 methylene units.

11. A composition according to claim 1 characterised in that the water-immiscible liquid contains a volatile silicone and optionally a non-volatile silicone and/or a non-silicone hydrophobic organic liquid selected from hydrocarbons, hydrophobic aliphatic esters, aromatic esters and hydrophobic alcohols.

12. A composition according to claim 1 wherein the water-immiscible liquid contains volatile silicone oil in an amount which is at least 10% by weight of the composition.

13. A composition according to claim 1 wherein the water-immiscible liquid comprises an alkyl benzoate, preferably in a proportion of up to 80% by weight thereof.

14. A composition according to claim 1 wherein the antiperspirant active comprises an aluminium and/or zirconium halohydrate, an activated aluminium and/or zirconium halohydrate, or an aluminium and/or zirconium complex or an activated aluminium and/or zirconium complex.

15. A composition according to claim 14 wherein the antiperspirant active comprises a halohydrate or complex in which aluminium and zirconium are both present.

16. A composition according to claim 1 wherein the proportion of antiperspirant active is from 5 to 40% by weight of the composition.

17. An antiperspirant product comprising a dispensing container having at least one aperture for outflow of the contents of the container and a composition according to claim 1 accommodated within the container.

18. A product according to claim 17 wherein the container has user operable parts for urging the contents of the container through its said outflow apertures.

19. A method of making a composition according to claim 1, comprising:

mixing the ingredients of the composition and, before or after complete mixing, heating the ingredients of the composition to a temperature at which continuous phase is a mobile liquid in which the organic polymer thickener (i) and the second structuring material (ii) are dissolved in the water-immiscible liquid, introducing the composition, at a temperature at which it is mobile, into containers, causing or allowing further cooling of the containers until the temperature of the composition in the containers has fallen below 30° C.

20. A method for preventing or reducing perspiration on human skin comprising topically applying to the skin a composition according to claim 1.

* * * * *